US005484810A

United States Patent [19]

Grisar et al.

[11] Patent Number: 5,484,810
[45] Date of Patent: Jan. 16, 1996

[54] TISSUE PROTECTIVE TOCOPHEROL ANALOGS

[75] Inventors: J. Martin Grisar, Wissembourg; Margaret A. Petty, Strasbourg, both of France; Frank Bolkenius, Kehl, Germany

[73] Assignee: Merrell Dow Pharmaceuticals Inc., Cincinnati, Ohio

[21] Appl. No.: 396,352

[22] Filed: Feb. 28, 1995

Related U.S. Application Data

[63] Continuation of Ser. No. 260,496, Jun. 15, 1994, abandoned, which is a continuation of Ser. No. 988,634, Dec. 10, 1992, abandoned.

[30] Foreign Application Priority Data

Jan. 2, 1992 [EP] European Pat. Off. ............. 92400006

[51] Int. Cl.$^6$ ..................... A61K 31/35; A61K 31/38; C07D 311/58; C07D 409/04
[52] U.S. Cl. ................. 514/456; 549/407; 549/60; 549/13; 549/9; 514/458; 514/444; 514/432; 514/431
[58] Field of Search .................... 549/407, 60, 13, 549/9; 514/458, 456, 444, 432, 431

[56] References Cited

U.S. PATENT DOCUMENTS

| | | |
|---|---|---|
| 3,419,560 | 12/1968 | Bernstein et al. . |
| 3,947,473 | 3/1976 | Scott et al. . |
| 4,153,796 | 5/1979 | Hoehn . |
| 4,214,081 | 7/1980 | Krapcho . |
| 4,237,162 | 12/1980 | Kabbe et al. . |
| 4,321,270 | 3/1982 | Sundeen . |
| 4,617,317 | 10/1986 | Bennet . |
| 4,694,090 | 9/1987 | Shiono et al. . |
| 4,728,650 | 3/1988 | Eziri et al. . |
| 4,975,457 | 12/1990 | Rupprecht et al. . |

FOREIGN PATENT DOCUMENTS

| | | |
|---|---|---|
| 0036169 | 9/1981 | European Pat. Off. . |
| 0236120 | 9/1987 | European Pat. Off. . |
| 0281261 | 9/1988 | European Pat. Off. . |
| 0293078 | 11/1988 | European Pat. Off. . |
| 0345593 | 12/1989 | European Pat. Off. . |
| 0369083 | 5/1990 | European Pat. Off. . |
| 0369874 | 5/1990 | European Pat. Off. . |
| 0387771 | 9/1990 | European Pat. Off. . |
| 0413668 | 2/1991 | European Pat. Off. . |
| 2634766 | 2/1990 | France . |
| 148173 | 7/1986 | Japan . |
| 148120 | 7/1986 | Japan . |
| 0215778 | 9/1990 | Japan . |

OTHER PUBLICATIONS

Journal of the Chemical Society, Perkin Transactions I, No. 9—Sep. 1979, Letchworth, GB, pp. 2124–2129—J. M. Akkerman et al.

Burger, Medicinal Chemistry, 2nd Edition, Interscience Publishers, Inc., New York, (1960) pp. 72–88.

Unanue et al., Text Book of Immunology, Williams & Wilkins, Baltimore, 1984, pp. 289–294.

Koyama et al., Chemical Abstracts, vol. 111, No. 13, 115639T (1989).

*Primary Examiner*—Nicky Chan
*Attorney, Agent, or Firm*—Carolyn D. Moon

[57] ABSTRACT

This invention relates to alkylated sulfonium alkylene derivatives of certain 2H-1-benzopyrans, to the intermediates and processes useful for their preparation, to their free-radical scavenger and cardioprotective properties and to their end-use application as therapeutic agents.

16 Claims, No Drawings

TISSUE PROTECTIVE TOCOPHEROL ANALOGS

CROSS-REFERENCE TO RELATED APPLICATION

This is a continuation of application Ser. No. 08/260,496, filed Jun. 15, 1994, abandoned; which is a continuation of application Ser. No. 07/988,634, filed Dec. 10, 1992, abandoned which is herein incorporated by reference.

This invention relates to alkylated sulfonium alkylene derivatives of certain 2H-1-benzopyrans, to the intermediates and processes useful for their preparation, to their free-radical scavenger and cardioprotective properties and to their end-use application as therapeutic agents.

More specifically this invention relates to alkylated sulfonium alkylene derivatives of the formula

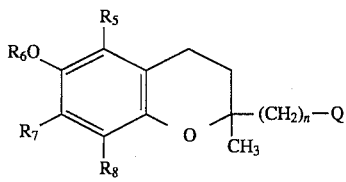   I the (R) and (S) enantiomers and racemic mixtures thereof, and the pharmaceutically acceptable salts thereof wherein Q is $S^{\oplus}R_1R_2 \cdot X^{\beta}$, X is a halide or $OS(O)_2R_3$, with $R_3$ being H, $C_{1-6}$ alkyl, $CF_3$, aryl or aralkyl, $R_1$ is $C_{1-6}$ alkyl, phenyl, benzyl or phenethyl, $R_2$ is $C_{1-6}$ alkyl, and $R_1$ and $R_2$ are a $C_4$– to $C_6$ alkylene which, together with the sulfur atom to which they are attached, form a 5—, 6— or 7-membered ring, $R_5$ is H or $C_{1-6}$ alkyl, $R_6$ is H or —C(O)R, R being H or $C_{1-9}$ alkyl, $R_7$ is H or $C_{1-6}$ alkyl, $R_8$ is H or $C_{1-6}$ alkyl and n is an integer of 1 to 6.

As used herein, the moiety $(CH_2)_n$ of Formula I wherein n is an integer of one to six represents a $C_{1-6}$ straight or branched-chain alkylene including such preferred species as methylene, ethylene, propylene, t-butylene, n-butylene, n-hexylene and isopropylene. The term "$C_{1-6}$ alkyl" includes the straight and branched-chain radicals having up to six carbon atoms with methyl, ethyl, propyl, n-butyl, t-butyl, pentyl and hexyl being representative. The term "—C(O)R" includes those acyl moieties wherein R is H and $C_{1-9}$ alkyl embracing formyl and the straight and branched-chain alkylcarbonyl moieties having up to ten carbon atoms including methylcarbonyl, ethylcarbonyl, propylcarbonyl, t-butylcarbonyl and n-hexylcarbonyl as preferred representatives. When used, aryl preferably is phenyl or phenyl substituted with $C_{1-6}$ alkyl radicals (e.g. toluene) and aralkyl is benzyl or phenethyl, the phenyl moiety of each optionally bearing lower $C_{1-6}$ alkyl radicals.

In the instance wherein $R_1$ and $R_2$, together with the sulfur atom to which they are attached form a 5 to 7 heterocycle, such moieties may be illustrated by

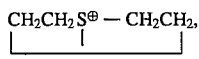

a thiophenium moiety, b

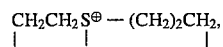

a thiopyrylium moiety, and b

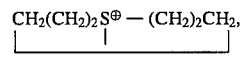

a thiopinium moiety, such compounds being named, for example, (if $X^{\ominus}$ is Br) tetrahydro-1-[2-(3,4-dihydro-6-hydroxy- 2,5,7,8-tetramethyl-2H-1-benzopyran-2-yl)ethyl] thiophenium bromide, tetrahydro-1-[2-(3,4-dihydro-6-hydroxy-2,5,7,8 -tetramethyl-2H-1-benzopyran-2-yl)ethyl] thiopyrylium bromide, and tetrahydro-1-[2-(3,4-dihydro-6-hydroxy-2,5,7,8 -tetramethyl-2H-1-benzopyran-2-yl)ethyl] thiopinium bromide.

The moiety "Q" includes tertiary sulfonium groups attached to the alkylene moiety. Although it is preferred to have the $R_1$ and $R_2$ radicals the same, the scope of this invention includes those derivatives wherein the $R_1$ and $R_2$ radicals are different. Preferably these radicals are methyl, ethyl, phenyl or benzyl.

The term "pharmaceutically acceptable salts" embraces those salts capable of being formed by the interaction of an organic or inorganic acid with a pharmaceutical base compound to yield a non-toxic pharmaceutically acceptable entity. Illustrative inorganic acids which form suitable salts include hydrochloric, hydrobromic, sulphuric and phosphoric acid and acid metal salts such as sodium mono-hydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid, 4-methylbenzenesulfonic acid and 2-hydroxyethane sulfonic acid. Either the mono- or the di-acid salts can be formed, and such salts can exist in either a hydrated or a substantially anhydrous form. In general, salts of these compounds are crystalline materials which are soluble in water and various hydrophilic organic solvents.

In general the compounds of Formula I may be prepared by standard chemical processes and techniques analogously known in the art. In practice, the preparation of the compounds of Formula I conveniently utilizes 3,4-dihydro-2H-1-benzopyran- 2-ols as starting materials which, for the most part, are known compounds. In those instances wherein any specific starting material is not known then such compounds may readily be prepared using the standard procedures analogously known in the art as well as by applying such processes as would be reasonably expected to produce the desired starting materials.

The preparation of the 3,4-dihydro-2,5,7,8-tetraalkyl- 2H-1-benzopyran-2-ols and their conversion to the final products of Formula I is depicted in the following reaction schemes.

Preparation of Intermediates

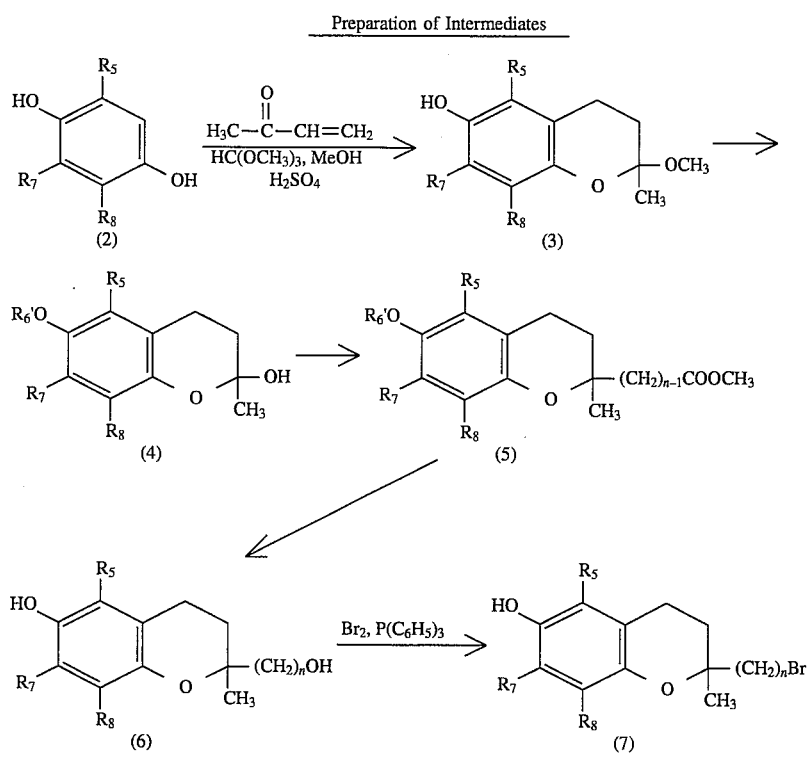

wherein R'$_6$ is —C(O)R, and R, R$_5$, R$_7$ and R$_8$ are as previously defined.

Preparation of final compounds

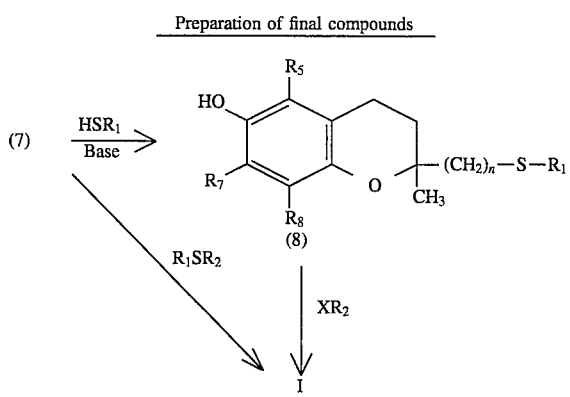

wherein n, R$_1$, R$_2$, R$_5$, R$_7$, R$_8$ and X are as previously defined.

The preparation of the intermediates start with the condensation of hydroquinones (2) with 3-butene-2-one in the presence of an acid, preferably sulfuric acid, the condensation being effected in methanol and trimethyl orthoformate. The so-produced dihydrobenzopyrans (3) are then sequentially subjected to acylation and hydrolysis reactions according to standard procedures to yield the hemiketals of Formula (4). Introduction of the hydroxyalkyl moiety at the 2-position of the compounds of Formula (4) can be effected by Witrig or Horner type reactions, preferably by reaction of the compounds of Formula (4) with a trimethylphosphonoester (e.g. trimethylphosphonoacetate) to yield the esters of Formula (5) which are hydrolyzed, and then reduced (preferably with lithium aluminum hydride) to yield the alcohols of Formula (6). These alcohols may also be formed directly by an acid catalyzed condensation of the hydroquinones (2) with the appropriate vinyl diols of Formulae (10) and (11).

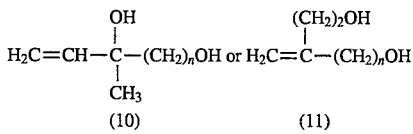

n being as defined above.

The alcohols of Formula (6) are converted to bromides of Formula (7) using standard conditions such as, for example, reaction with bromotriphenylphosphonium bromide (Ø$_3$PBr$^+$Br$^-$), obtained by reaction of triphenylphosphine with bromine in dichloromethane. The bromides of Formula (7) may be converted to the desired tertiary sulfonium derivatives of Formula I, utilizing standard procedures well known in the art. For example, the reaction of a bromide of Formula (7) with equimolar or excess quantities of an appropriate disulfide (R$_1$SR$_2$) under pressure at temperatures of about 90°–150° C. with or without a solvent may be utilized. Alternatively, the disulfide (8) may be prepared and subsequently S-alkylated with the appropriate alkyl halide or alkyl sulfonate (i.e., R$_2$X, wherein X is a halide or alkylsulfonate —OS(O)$_2$R$_3$). Standard procedures well known in the art may be used in the preparation of the disulfides of Formula (8). For example, the bromide (7) may be reacted with the sodium or potassium salt of a mercaptan, HSR$_1$, in an inert solvent, preferably dimethylformamide at 25°–100° C. for 2 to 48 hours to give, after appropriate work-up, the disulfides (8). S-alkylation of the disulfides of Formula (8) can be accomplished by a number of procedures known to the art. For example, refluxing a solution of a disulfide of Formula (8) and an alkyl ester of p-toluenesulfonic acid will result in the corresponding sulfonium compound of Formula I, wherein X⁻ = 4—CH₃C₆H₄S(O₂)O⁻. When an alkyl halide (R₂X) is used in this reaction, it is often advantageous to also add an equimolar amount of silver tetrafluoroborate; after removal of silver halide, the tetrafluoroborate salt of the sulfonium compound is obtained. When perchloric acid is used instead of silver tetrafluoroborate, it is necessary to protect the 6-OH group by acylation ($R_5$=—C(O)R). The conversion of perchlorate or tetrafluoroborate salts of compounds of Formula I to pharmaceutically acceptable salts is feasible but tedious and therefore not preferred.

In those instances wherein it is desired to prepare the esters of Formula I [i.e., $R_6$ represents —C(O)R], acylation of the 6-OH moiety may be accomplished by acylating compounds of Formula (8) using standard procedures well known in the art, such as by treatment of the alcohol with the appropriate acid anhydride or acyl halide. Alternatively, the acylation may be accomplished as the final step.

Further, as there is an asymmetric carbon atom at the 2-position, the compounds may occur as either the R- or the S-enantiomers, or mixtures thereof. The preparation of the individual enantiomeric form may be effected by resolving the acids of Formula (5) by standard and conventional means such as, for example, via the use of diastereomeric salts with optically active amines, or alternatively, by resolving the alcohols (7) as esters with optically active acids, e.g. L-2,4-MeClC₆H₃CHMeCOOH (Me representing methyl).

The following examples will serve to illustrate the techniques and processes described herein.

EXAMPLE 1

3,4-Dihydro-2-(2-bromoethyl)-2,5,7,8-tetramethyl-2H-1-benzopyran-6-ol

To 11.0 g (0.042 mol) of triphenylphosphine in 200 ml of dichloromethane is added dropwise a solution of 6.71 g (0.042 mol) of bromine in 50 ml of dichloromethane. The solution is stirred for 30 min at room temperature, then 10.0 g (0.04 mol) of 3,4-dihydro-6-hydroxy-2,5,7,8-tetramethyl-2H-1-benzopyran-2-ethanol (CAS 79907-48-5) is added. The resulting solution is refluxed for 4 hours, allowed to cool overnight, washed with a solution of 15 g of sodium carbonate in 200 ml of water, dried over anhydrous sodium sulfate, filtered and evaporated. The resulting oil is crystallized from methanol to give 9.22 g of 3,4-dihydro-2-(2-bromoethyl)-2,5,7,8-tetramethyl-2H-1-benzopyran-6-ol.

The optically active enantiomers are obtained by substituting racemic 3,4-dihydro-6-hydroxy-2,5,7,8-tetramethyl-2H-1-benzopyran-2-ethanol with enantiomer R- (CAS 94425-68-0) or S- (CAS 94425-67-9) and by following the procedures of this example for each individual isomer.

EXAMPLE 2

3,4-Dihydro-2-(2-methylthioethyl)-2,5,7,8-tetramethyl-2H-1-benzopyran-6-ol

A mixture of 6.26 g (0.02 mol) of 3,4-dihydro-2-(2-bromoethyl)-2,5,7,8-tetramethyl-2M-1-benzopyran-6-ol and 2.80 g (0.04 mol) of sodium thiomethoxide in 50 ml of dry dimethylformamide is stirred at 70° C. for 16 hours. Water and 2N hydrochloric acid is added and the product is extracted with ethyl acetate. The extract is washed with water and with a sodium bicarbonate solution, dried over anhydrous sodium sulfate, filtered and evaporated. The resulting product is recrystallized from ethyl acetate/heptane to give 2.90 g of the title compound, m.p. 66.5°–67° C. Utilizing the R- and the S-enantiomers, as prepared in Example 1, the corresponding enantiomers are similarly prepared by following the procedure described in this example.

EXAMPLE 3

[2-(3,4-Dihydro-6-hydroxy-2,5,7,8-tetramethyl-2H-1-benzopyran-2-yl)ethyl)-dimethylsulfonium 4-methylbenzenesulfonate A solution of 2.90 g of 3,4-dihydro-2-(2-methylthioethyl)-2,5,7,8-tetramethyl-2H-1-benzopyran-6-ol and 2.12 g (10% excess) of methyl 4-methylbenzenesulfonate in 30 ml of acetonitrile is refluxed for 48 hours. On cooling and addition of ethylacetate, the product crystallizes and is recrystallized from the same solvent pair, 4.19 g (87% yield), m.p. 156°–158° C., identified by elemental analysis, IR, UV and ¹H and ¹³C NMR spectra.

EXAMPLE 4

[2-(3,4-Dihydro-6-hydroxy-2,7,8-trimethyl-2H-1-benzopyran-2yl)ethyl]-dimethylsulfonium 4-methylbenzenesulfonate Following the procedures described in Examples 1 to 3, but using 3,4-dihydro-6-hydroxy-2,7,8-trimethyl-2M-1-benzopyran-2-ethanol (CAS 93600-70-5) as starting material, the title compound is obtained.

EXAMPLE 5

[2-(3,4-Dihydro-6-hydroxy-2,5,8-trimethyl-2H-1-benzopyran-2-yl)ethyl]-dimethylsulfonium 4-methylbenzenesulfonate Following the procedures described in Examples 1 to 3, but using 3,4-dihydro-6-hydroxy-2,5,8-trimethyl-2M-1-benzopyran-2-ethanol (CAS 93600-69-2) as starting material, the title compound is obtained.

EXAMPLE 6

[2-(3,4-Dihydro-6,hydroxy-2,5,7-trimethyl-2H-1-benzopyran-2 yl)ethyl]-dimethylsulfonium 4-methylbenzenesulfonate Following the procedures described in Examples 1 to 3, but using 3,4-dihydro-6-hydroxy-2,5,7-trimethyl-2H-1-benzopyran-2-ethanol (CAS 93600-68-1) as starting material, the title compound is obtained.

EXAMPLE 7

[3-(3,4-Dihydro-6-hydroxy-2,5,7,8,-tetramethyl-2H-1-benzopyran-2-yl) propyl]-dimethylsulfonium 4-methylbenzenesulfonate Following the procedures described in Examples 1 to 3, but using 3,4-dihydro-6-hydroxy-2,5,7,8-tetramethyl-2H-1-benzopyran-2-propanol (CAS 104568-57-2) as starting material, the title compound is obtained.

EXAMPLE 8

Resolution of 3,4-Dihydro-6-hydroxy-2,5,7,8-tetramethyl-2H-1-benzopyran-2-acetic Acid To a hot solution of 132.16 g of the title compound in 700 ml of isopropanol is added 60.59 g of S-(−)-α-methylbenzylamine and 100 ml of ethyl acetate. Slow crystallization overnight in a refrigerator gives somewhat more than half the theoretical amount of crystalline material (checked by evaporating the filtrate to dryness). This material is recrystallized in a like manner three times and the resulting pure diastereomeric salt is converted to free acid by shaking in 200 ml of 2N hydrochloric acid and 400 ml of ethyl acetate. The aqueous phase is separated and extracted with ethyl acetate. The combined organic phase is washed with 2N hydrochloric acid, water, and a saturated sodium chloride solution, dried over anhydrous sodium sulfate, filtered and evaporated to dryness. The resulting solid is recrystallized from ethyl acetate/heptane to give 40.85 g (62%) of the S-(−)-enantiomer of the title compound, $\alpha_D^{25}=-9.61°$ (0.95% in MeOH). The enantiomeric purity, as determined by HPLC is ee=99.9%. Elemental analysis was within 0.3% of theory.

The combined filtrates of the above diastereomeric salt crystallizations are evaporated and converted to free acid as described to give 92.02 g of material. It is dissolved in 600 ml of isopropanol and 42.19 g of R-(+)-α-methylbenzylamine is added as well as 200 ml of ethyl acetate. Slow crystallization and two recrystallizations give, after conversion to free acid and one final recrystallization, 41.50 g (63%) of the R-(+)-enantiomer of the title compound, $\alpha_D^{25}=+9.35°$ (0.96% in MeOH) ee=99.9%. Anal. C,H.

It is possible to recover the unresolved balance of material from the filtrates as well as the enantiomeric amines for use in a subsequent resolution.

EXAMPLE 9

2S-(−)- and 2R-(+)-[2-(3,4-Dihydro-6-hydroxy-2,5,7,8-tetramethyl-2H-1-benzopyran-2-yl)-ethyl]-dimethylsulfonium 4-methylbenzenesulfonate To a stirred solution of 38.91 g of the S-(−)-enantiomer of the acid described in the preceding example in 500 ml of tetrahydrofuran is added 30 ml of 10M borane methylsulfide complex over 30 minutes and the mixture is stirred at reflux temperature for 3 hours. After cooling, 120 ml of methanol is added dropwise and the resulting solution is evaporated to dryness. The residue is taken up in ethyl acetate, washed with 2N hydrochloric acid, water, saturated sodium bicarbonate and sodium chloride solutions, dried over anhydrous sodium sulfate, filtered and evaporated. The residue is recrystallized from ethyl acetate/heptane to give 30.69 g (83%) of 2-S-(−)-3,4-dihydro-6-hydroxy-2,5,7,8-tetramethyl-2M-1-benzopyran-2-ethanol, $\alpha_D^{25}=-6.44°$ (0.90% in MeOH). The 2R-(+)-enantiomer of this compound is obtained in a like fashion from the R-(+)-enantiomer of the acid described in the preceding example. Its rotation is +6.00° (1.01% in MeOH).

These two enantiomeric alcohols are each converted to the bromide, methylsulfide, and dimethylsulfonium tosylate by the procedures described in Examples 1, 2, and 3 to give the title compounds as 2S-(−)-enantiomer, $\alpha_D^{25}=-18.74°$ (0.95% in MeOH), ee=99.9% and 2R-(+)-enantiomer, $\alpha_D^{25}=18.24°$ (1.19% in MeOH), ee=99.9%.

Having described the scope of the compounds of this invention as well as the generic and specific methods for preparing said compounds, the following information describes the utility, and the methods therefor, of the compounds of this invention.

The compounds of this invention are free radical scavengers. Free radical reactions have been implicated in the pathology of more than 50 human diseases. Radicals and other reactive oxygen species are formed constantly in the human body both by deliberate synthesis (e.g. by activated phagocytes) and by chemical side-reactions. They are removed by enzymic and non-enzymic antioxidant defence systems. Oxidative stress, occurring when antioxidant defences are inadequate, can damage lipids, proteins, carbohydrates and DNA. A few clinical conditions are caused by oxidative stress, but more often the stress results from the disease and can make a significant contribution to the disease pathology. For a more detailed review see B. Halliwell in *Drugs*, 1991, 42, 569–605.

When the blood supply to parts of the heart muscle is blocked, a myocardial infarct (heart attack) results and the deprived muscle tissue dies with the result of permanent heart damage. If the blood supply can be re-established within hours after ischemia, the heart muscle tissue remains viable and permanent damage can be reduced. This can be accomplished by surgical as well as pharmacologic (thrombolysis) procedures and these processes are known as reperfusion.

Ischemia followed by reperfusion causes formation of oxygen-derived free radicals and increased lipid peroxidation and results in tissue injury. Administration of free radical scavengers to animals subjected to ischemia followed by reperfusion reduces these effects in heart, lung, kidney, pancreas, brain and other tissues.

Reperfusion is now widely and successfully applied and it has been claimed that fatalities due to myocardial infarction can be reduced by 20–30%. However, reperfusion also poses problems. Oxygen-deprived (ischemic) tissue finds itself in an abnormal state and is vulnerable when suddenly exposed to oxygen-rich blood. This has been termed the "oxygen paradox" and leads to reperfusion damage in the form of cell death. It has been postulated that this damage is due to oxygen-derived free radicals. Evidence for this hypothesis has been obtained in animal experiments. B. R. Lucchesi and coworkers showed that the enzyme superoxide dismutase, as well as the free radical scavenger N-(mercaptopropionyl)-glycine reduce canine myocardial reperfusion injury (Cir. Res., 1984, 54, 277–285; J. Cardiovasc. Pharmacol., 1986, 8, 978–88; Fed. Proc., 1987, 46, 2413–21).

Vitamin E, i.e., α-tocopherol, a well known compound of the formula

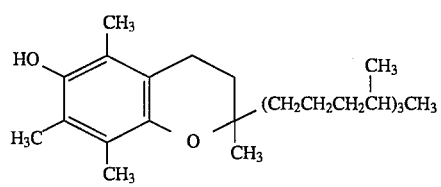

is a natural anti-oxidant that reacts with oxygen-derived free radicals as well as hydrogen peroxide. It has been shown that it is intercalated in lipid membranes and that its biological function is to protect biomembranes against oxidative attack. The anti-oxidant 3,4-dihydro-2,5,7,8-tetramethyl-2H-2-benzopyran-6-ol moiety of α-tocopherol is constantly regenerated by the ubiquitous redox systems.

The compounds of this invention also possess a related or similar 3,4-dihydroxy-2,5,7,8-tetraalkyl-2H-1-benzopyran-2-yl moiety, but the 2-position lipophilic moiety of the α-tocopherol molecule, which is thought to be responsible for its ubiquitous incorporation into biomembranes, is replaced with a hydrophilic moiety to impart a greater bio-availability. For example, certain compounds of the present invention have shown an affinity for cardiac tissue. Thus, the compounds of this invention are also useful as pharmacologic anti-oxidants and free radical scavengers and as scavengers of superoxyl anion radical $O_2^-$. They can be therapeutically employed where reperfusion damage due to oxygen-derived free radicals and hydrogen peroxide causes cell death in tissues. This situation arises when total or partial blockade of blood supply to tissues is removed, either spontaneously (transient ischemia) or by pharmacologic or surgical intervention (thrombolysis, angioplasty, by-pass, organ transplant and the like). Tissues subjected to transient ischemia or reperfusion in various disease states, or by their medical treatment, are those of heart, lung, kidney, pancreas and brain. In particular, the now rapidly increasing practice of pharmacologic thrombolysis to induce reperfusion after coronary infarct and stroke, will benefit by prior or concomitant administration of a free radical scavenger such as the compounds of this invention. Similarly, surgical interventions, such as percutaneous transluminal coronary angioplasty, where a dilating balloon is used to increase the luminal diameter in severely occluded atherosclerotic vessels, coronary by-pass operations, and organ transplant surgery create conditions where reperfusion damage due to oxygen-derived radicals takes place and can be reduced by scavengers. Transient ischemia is one of the causative factors that lead to angina pectoris, and thus the compounds of this invention are also useful as antianginal agents.

The process of inflammation is also known to involve the release of superoxyl radicals from phagocytic cells which cause some of the symptoms of rheumatoid arthritis and other inflammatory diseases such as ulcerative colitis and inflammatory dermatological disorders such as psoriasis. Of particular use of this anti-inflammatory effect of the compounds of this invention is in the treatment of inflammatory lower bowel disease.

Inhalation injury of the lungs is typically caused by heat and chemical irritation, and chemical injury is the leading lethal cause of smoke inhalation injury. Smoke inhalation leads to lung injury due to an increase in pulmonary microvasculature and pulmonary edema. This process is accompanied by increased lipid peroxidation in lung tissue. An inhibitor of lipid peroxidation was shown to reduce these symptoms in animals subjected to hot sawdust smoke by Z. Min et al., (*J. Med. Cell. PLA,* 1990, 5, (2) 176-180). They suggest the use of antioxidants in treatment of smoke inhalation-lung injury, adult respiratory distress syndrome, emphysema and asthma.

Reactive oxygen species also play a role in the formation of foam cells in atherosclerotic plaques (reviewed by D. Steinberg et al., *New Engl. J. Med.,* 1989, 328, 915–924) and the free radical scavenger probucol has a marked anti-atherosclerotic effect in hyperlipidemic rabbits (Carew et al., *Proc. Nat. Acad. Sci. USA,* 1987, 84, 7725–7729. Degenerative retinal damage and diabetogenic retinopathy have also been listed as target for treatment with free radical scavengers (cf. J. W. Baynes, *Diabetes,* 1991, 40, 405–412; S. P. Wolff et al., *Free Rad. Biol. Med.,* 1991, 10, 339–352).

The compounds may also be useful in the treatment of cancers, and degenerative diseases related to aging, stroke, and head trauma, since oxygen-derived free radicals have been identified among causative factors. For reviews, see B. Halliwell and C. Gutteridge, Biochem. J., 1984, 219, 1–14; TINS 1985, 22-6. Antioxidants have also been shown to be useful in the treatment of cataracts, *Free Rad. Biol. Med.,* 12:251–261 (1992)

In vitro and in vivo activity for the compounds of this invention may be determined by the use of standard assays which demonstrate the free radical scavenging property, affinity for cardiac tissue and cardioprotective properties, as well as by comparison with agents known to be effective for these purposes.

Exemplary of the assay useful for determining the free-radical scavenging property of the compounds of this invention is by the in vitro inhibition of lipid peroxidation in rat brain homogenates.

The free radical scavenging property may also be evaluated by an assay wherein superoxide radicals are generated by 4 mU of xanthine oxidase in the presence of 0.1 mM xanthine and detected by reduction of 40 μM nitro blue tetrazolium (NBT) to the diformazan dye in a spectrophotometric assay as described by C. Beauchamp and I. Fridovick, (*Analyt. Biochem.* 1971, 44, 276–287). 30 U of superoxide dismutase inhibited this reduction by 90% which is due to superoxide radicals. In the presence of a superoxide scavenger (test compound) there is a competition for the superoxide radical and thus a reduction in the color formation of NBT demonstrates the superoxide radical scavenging property of the test compound.

Inhibiting the process of lipid peroxidation may be assayed using tissue homogenates for measuring the antioxidant activity of biological fluids by the methodology of J. Stocks et al., (*Clin. Sci. Mol. Med.,* 1974, 47, 215–222), wherein a brain tissue homogenate of untreated adult Sprague Dawley rats is utilized.

Samples of total volume 1 ml of diluted brain homogenate and with the scavenger at an appropriate dilution are incubated. Non-incubated samples are taken as background. Controls are run without scavenger and a sample containing only buffer is taken as blank. After incubation at 37° C. for 30 minutes, 200 μl of 35% perchloric acid is added, the samples centrifuged and 800 μl of the supernatants mixed with 200 μl of 1% thiobarbituric acid. The pink condensation product of thiobarbituric acid reactive material is developed at 100° C. in a boiling water bath for 15 minutes, and absorbance read at 532 nm.

For ex vivo inhibition of tissue including heart tissue, lipid peroxidation in mice may be utilized to demonstrate the ability of the compounds to penetrate and act as free radical scavengers in these tissues. This assay involves pretreatment of male CD1 mice by subcutaneous administration of the test compound. One hour later the tissues are excised, homogenized 1+9 (w/v) in 20 mM potassium phosphate buffer at pH 7.3 (0.14M KCl) and incubated at 1/100 concentration in 1 ml of buffer at 37° C. for 30–120 minutes. At the end of the incubation 200 μl of 35% perchloric acid is added and proteins removed by centrifugation. To 800 ml of the supernatant are added 200 μl of 1% TBA and the samples are treated to 100° C. for 15 minutes. The TBA-adduct is extracted into 2 times 1 ml of n-butanol. The fluorescence is measured at an excitation wavelenght of 515 nm and an emission wavelength of 553 nm against a standard prepared from malondialdehyde dimethylacetal.

Stimulated human leukocytes release superoxyl radicals and other oxygen metabolites, which, during inflammation, act as microbicidal agents. At the same time, they release proteolytic enzymes, such as elastase, which are also microbicidal but potentially threaten the connective tissue of the host. The endogenous $\alpha_1$-proteinase inhibitor ($\alpha_1$Pi) normally protects the host tissue from proteolytic digestion. $\alpha_1$Pi is however, inactivated by the leukocyte-derived oxidants. Antagonism of the oxidant formation and hence of the pro-inflammatory inactivation of $\alpha_1$Pi is achieved with the disclosed radical scavengers. The concentration needed to protect 50% of the elastase inhibitory capacity of $\alpha_1$Pi ($PC_{50}$) depends on the amount of stimulated leukocytes present.

Method: The procedure described by Skosey and Chow was followed (see J. L. Skosey and D. C. Chow in *Handbook of Methods for Oxygen Radical Research* (Greenwald, R. A., ed.) 1985, pp. 413–416, CRC Press, Boca Raton). In short, human $\alpha_1$Pi was incubated with zymosan-stimulated human peripheral-blood leukocytes in the absence or presence of the scavengers. The amount of $\alpha_1$Pi protected from oxidative inactivation was determined by its residual elastase inhibitory capacity.

The relevance to inflammation matter has been reviewed by Weiss (see S. J. Weiss, *N. England J. Med.*, 1989, 320, 365–376). Lung emphysema is associated with a genetic defect in $\alpha_1$Pi; the disease is further enhanced by oxidants inhaled during cigarette smoking, which leads to oxidative inactivation of $\alpha_1$Pi in the lung tissue (see J. Travis and G. S. Salvesen, *Annu. Rev. Biochem.*, 1983, 52, 655–709). Oxidized $\alpha_1$Pi has also been isolated from rheumatoid synovial fluid (see P. S. Wong and J. Travis, *Biochem. Biophys. Roc. Commun.*, 1980, 06, 1440–1454). The degradation of hyaluronic acid, a macromolecule accounting for the viscosity of synovial fluid, is triggered by superoxyl radicals released from human leukocytes in vitro (see R. A. Greenwald and S. A. Moak, *Inflammation*, 1986, 10, 15–30). Furthermore, nonsteroidal anti-inflammatory drugs were shown to inhibit the release of superoxyl radicals from leukocytes (see H. Strom and I. Ahnfelt-Ronne, *Agents and Actions*, 1989, 26, 235–237 and M. Roch-Arveiller, V. Revelant, D. Pharm Huy, L. Maman, J. Fontagne, J. R. J. Sorenson and J. P. Giroud, *Agents and Actions*, 1990, 31, 65–71), and 5-aminosalicylic acid exerts its therapeutic activity in inflammatory bowel disease by a radical scavenger mechanism (see I. Ahnfelt-Ronne, O. H. Nielsen, A. Christensen, E. Langholz, V. Binder and P. Riis, *Gastroenterology*, 1990, 98, 1162–1169). Therefore, it is believed that the compounds of this invention are useful in the mentioned pathologic situations and that inflammatory bowel disease may be a special target. An immune stimulatory effect of antioxidants has also been reported in that they enhanced lymphocyte activity (R. Anderson and P. T. Lukey, *Ann. N. Y. Acad. Sci.*, 1987, 498, 229–247) in vitro in the presence of triggered leukocytes, and ex vivo after pretreatment of human volunteers.

Thus, using standard and well known methodology, as well as by comparison with known compounds found useful, it is to be found that the compounds are free radical scavengers useful in the prevention and treatment of such disease states related to neurotoxicity due to excessive glutamate release, to Huntington's disease, Alzheimer's disease and other cognitive dysfunctions, (e.g. memory, learning and attention deficits), amnesia, and Parkinson's disease, as well as the treatment and prevention of tissue damage in heart, lung, kidney, pancreas and brain tissues induced by ischemia/reperfusion, and to allay acute blood loss due to haemorrhagic shock.

Most preferably, the compounds are administered intravenously particularly under crisis situations wherein it is essential that the therapeutic agent be delivered to its site of action as quickly as possible, such as in those emergency conditions caused by coronary infarction, stroke and surgical interventions, conditions which can cause severe reperfusion damage.

The compounds of this invention can be utilized both prophylactically and therapeutically. The term "treat" or forms thereof means to prevent or alleviate the patients' disease or condition. The term "patient" refers to a warm-blooded animal such as, for example, rats, mice, dogs, cats, guinea pigs, primates, and humans. The amount of active ingredient for therapeutic administration can vary over a wide range and is dependent upon such factors as the species of mammal to be treated, its age, health, sex, weight, nature and the severity of the condition being treated. Generally, a therapeutically effective amount of the active ingredient to be administered will range from about 0.1 mg/kg to 30 mg/kg of body weight per day. For prophylactic administration, corresponding lower doses can be utilized.

The compounds of this invention can also be orally administered, preferably using more active ingredient per day than when parenterally administered, preferably taking divided doses 3 to 4 times per day. Preferably, enteral administration in post "crisis" situations, particularly after release from hospitalized conditions. The compounds can be used in standard dosage unit forms such as tablets, capsules, dragees, lozenges, elixirs, emulsions, suspensions, and in cases wherein topical application is preferred by suppository or sub-lingual administration. Tablets and capsules containing from 25 to 400 mg of active ingredient are preferred modes of enteral administration. Of course, in the treatment of inflammation the preferred method of administration is by depot injection directly to the situs of the inflammation area with follow-up enteral means of administration.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and which prevent adhesion of tablet material to the surfaces of tablet dies and punches. Suitable lubricants include, for example, talc stearic acid, calcium stearate, magnesium stearate and zinc stearate. Also included within the definition of a pharmaceutical carrier as used herein, are disintegrating agents added to assist the breakup and dissolution of tablets following administration, as well as stabilizers (e.g., ascorbic acid), coloring and/or flavoring agents to enhance the qualities of the tablets.

Suitable liquid excipients for the preparation of liquid dosage unit forms include water and alcohols such as ethanol, benzyl alcohol and the polyethylene glycols, either with or without the addition of a surfactant. In general, the preferred liquid excipients, particularly for injectable preparations, include water, physiological and saline solutions, dextrose and glycol solutions such as an aqueous propylene glycol or polyethylene glycol solutions. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. In certain topical and parenteral preparations, various oils can be utilized as carriers or excipients. illustrative of such oils are mineral oils, glyceride oils such as lard oil, cod liver oil, peanut oil, sesame oil, corn oil and soybean oil. For insoluble compounds, suspending agents may be added as well as agents to control the viscosity, as for example, magnesium aluminum silicate or carboxymethylcellulose. In addition to these excipients, buffers, preservatives and emulsifying agents may also be added.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The compounds of the present invention may be incorporated into an aerosol preparation by means commonly known to those skilled in the art. The aerosol preparation may be prepared for use as a topical aerosol or may be prepared for inhalation. The aerosol preparation may be in the form of a solution or suspension and may contain other ingredients such as solvents, propellants and/or dispersing agents. Typical examples of aerosol preparations are shown in *Remington's Pharmaceutical Sciences*, 18th ed., Mack Publishing Company, Easton Pennsylvania, pp. 1694–1712(1990) incorporated herein by reference.

Of course, as is true in most instances wherein certain classes of chemical compounds have been found to have beneficial therapeutic end-use applications, certain sub-generic groups and certain specific compounds are preferred.

In this instance the preferred compounds of Formula I are those wherein $R_5$, $R_7$ and $R_8$ are $C_{1-6}$ alkyl and more preferably methyl; wherein $R_6$ is H, formyl, methyl carbonyl, t-butylcarbonyl, ethylcarbonyl, propylcarbonyl, pentylcarbonyl; wherein n is 2 (representing an ethylene moiety) and the substituents attached to the sulfur atom are methyl or ethyl.

Of course, it is obvious that the 2-position methyl moiety may be removed or replaced with another $C_{1-6}$ alkyl (e.g., the 2-position methyl may be replaced with H, ethyl, propyl, butyl and the like). Such so-modified compounds are also contemplated within the scope of this invention for the utilities herein alleged, and may be prepared by standard procedures obvious to those skilled in the art.

What is claimed is:

1. A compound of the formula

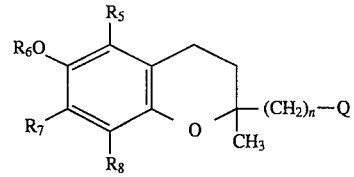

the (R) or (S) enantiomer or racemic mixture thereof, or the pharmaceutically acceptable salt thereof wherein Q is $S^\oplus R_1 R_2 . X^\ominus$, X is a halide or $OS(O)_2 R_3$, with $R_3$ being $C_{1-6}$ alkyl, $CF_3$, aryl or aralkyl, $R_1$ is $C_{1-6}$ alkyl, phenyl, benzyl or phenethyl, $R_2$ is $C_{1-6}$ alkyl, or $R_1$ and $R_2$ are a $C_{4-}$ to $C_6$ alkylene which, together with the sulfur atom to which they are attached, form a 5-, 6- or 7-membered ring, $R_5$ is H or $C_{1-6}$ alkyl, $R_6$ is H or —C(O)R, R being H or $C_{1-9}$ alkyl, $R_7$ is H or $C_{1-6}$ alkyl, $R_8$ is H or $C_{1-6}$ alkyl and n is an integer of 1 to 6.

2. The compound of claim 1 wherein $R_1$ and $R_2$ are each $C_{1-6}$ alkyl.

3. The compound of claim 2 wherein $R_1$ and $R_2$ are each methyl.

4. The compound of claim 1 wherein $R_5$ is $C_{1-6}$ alkyl.

5. The compound of claim 4 wherein $R_5$ is methyl.

6. The compound of claim 1 wherein $R_6$ is hydrogen.

7. The compound of claim 1 wherein $R_7$ is $C_{1-6}$ alkyl.

8. The compound of claim 7 wherein $R_7$ is methyl.

9. The compound of claim 1 wherein $R_8$ is $C_{1-6}$ alkyl.

10. The compound of claim 9 wherein $R_8$ is methyl.

11. The compound of claim 1 wherein X is $OS(O)_2 R_3$ and wherein $R_3$ is an aryl moiety.

12. The compound of claim 1 wherein the compound is [2-(3,4-dihydro-6-hydroxy-2,5,7,8-tetramethyl-2H-1-benzopyran-2-yl)ethyl]dimethylsulfonium, 4-methylbenzenesulfonate.

13. The compound of claim 12 in the R form enantiomer.

14. The compound of claim 12 in the S form enantiomer.

15. A pharmaceutical composition comprising a compound of claim 1 and a pharmaceutically acceptable carrier.

16. A method of treating a patient for reperfusion damage by administering an effective amount of a compound of claim 1.

* * * * *

UNITED STATES PATENT AND TRADEMARK OFFICE
CERTIFICATE OF CORRECTION

PATENT NO. : 5,484,810
DATED : January 16, 1996
INVENTOR(S) : J. Martin Grisar et al.

It is certified that error appears in the above-identified patent and that said Letters Patent is hereby corrected as shown below:

At column 1, line 30, the patent reads "X$^\beta$" and should read -- X$^\ominus$ --.
At column 2, line 1, and again at line 7, the patent reads "b" and should read --by--.
At column 3, line 62, the patent reads "Witrig" and should read --Wittig".
At column 6, line 41, the patent reads "-2M-" and should read -- -2H- --.
At column 9, line 60, the patent reads "328" and should read --320--.

Signed and Sealed this

Twenty-fourth Day of September, 1996

Attest:

BRUCE LEHMAN

*Attesting Officer*     *Commissioner of Patents and Trademarks*